United States Patent [19]
Krbechek et al.

[11] Patent Number: 5,457,236
[45] Date of Patent: Oct. 10, 1995

[54] PROCESS FOR THE PRODUCTION OF BETA-DIKETONE

[75] Inventors: Leroy O. Krbechek, Santa Rosa, Calif.; Mary I. Casey, Bishopstown, Islamic Rep. of Ireland

[73] Assignee: Henkel Corporation, Plymouth Meeting, Pa.

[21] Appl. No.: 207,434

[22] Filed: Mar. 7, 1994

[51] Int. Cl.$^6$ .................................... C07C 45/45
[52] U.S. Cl. ............................................. 568/314
[58] Field of Search ............................... 568/314

[56] References Cited

U.S. PATENT DOCUMENTS

| | | | |
|---|---|---|---|
| 4,028,417 | 6/1977 | Muller et al. | 568/314 |
| 4,175,012 | 11/1979 | McKay et al. | 204/108 |
| 4,387,089 | 6/1983 | De Polo | 568/314 |
| 4,482,245 | 11/1984 | Maulding | 568/314 |
| 4,562,067 | 12/1985 | Hopp et al. | 568/314 |
| 5,015,777 | 5/1991 | Chisolm et al. | 568/314 |

FOREIGN PATENT DOCUMENTS

| | | | |
|---|---|---|---|
| 454624 | 10/1991 | European Pat. Off. | 568/314 |

*Primary Examiner*—James H. Reamer
*Attorney, Agent, or Firm*—Ernest G. Szoke; Wayne C. Jaeschke; Patrick J. Span

[57] ABSTRACT

In a process for preparing betadiketones which comprises an alkaline condensation of an ester and an acetophenone in the presence of an alkaline catalyst in an inert organic solvent, the improvement comprising at least one of the following conditions:

(i) adding the acetophenone to the reaction mixture in a time period sufficiently short whereby degradation products in the reaction mixture are minimized;

(ii) at the completion of the reaction, adding additional solvent to rapidly decrease the temperature of the reaction product mixture.

(iii) mixing the organic solvent phase with the aqueous acid phase in the acidification step for a time period sufficiently long whereby the concentration of alkali metal remaining in the organic solvent phase is substantially zero; and (iv) decreasing the time between the completion of the acetophenone addition step and the initiation of the acidification step.

6 Claims, No Drawings

PROCESS FOR THE PRODUCTION OF BETA-DIKETONE

BACKGROUND OF THE INVENTION

1. Field of the Invention

This invention relates to improvements in the process of preparation of beta-diketones and in particular to the production of 1-phenylisodecane-1,3-dione by the alkaline condensation of acetophenone and an ester of an alkanoic acid.

2. Statement of Related Art

U.S. Pat. No. 4,175,012 to Kenneth MacKay et al., describes the preparation of beta-diketones which are useful as metal extractants. The diketones have the formula

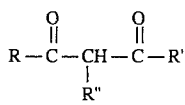

where R is phenyl or alkyl substituted phenyl, R' is alkyl, alkyl substituted phenyl or chloro substituted phenyl, and R" is H or CN. The products are prepared by the reaction of a compound having an acetyl moiety and a lower alkyl ester in the presence of sodium hydride and an inert organic solvent.

In recent time the beta-diketone, 1-phenyl isodecane-1,3-dione has been prepared by the alkaline condensation of acetophenone and a lower alkyl ester of an alkanoic acid such as methyl isooctanoate in an inert organic solvent media. In the reaction some of the methyl isooctanoate is converted to sodium isooctanoate. When the reaction is completed, the reaction mixture is acidified, typically in a separate reactor which contains excess sulfuric acid, whereby the sodium salts are acidified. The resultant acidified organic phase is then washed several times with water, and the diketone product recovered by stripping the volatiles from the organic and distilling the residue at reduced pressure.

The foregoing process, however, has some disadvantages which results in low yields and some residual degradation products. These result from the fact that the diketone product is thermally cleaved in the presence of alkali to a carboxylic acid and a methyl ketone degradation product. Accordingly it is desirable that the process be improved so that yield of product is maximized and the formation of degradation products is minimized.

DESCRIPTION OF THE INVENTION

Other than in the operating examples, or where otherwise indicated, all numbers expressing quantities of ingredients or reaction conditions used herein are to be understood as modified in all instances by the term "about".

Since the preferred product of interest in the present invention is 1-phenylisodecane-1,3-dione the invention will be described with respect to such product. However, the invention is applicable to the preparation of other diketone products in which a lower alkyl ester of an organic carboxylic acid, preferably an alkanoic acid, is reacted with a compound containing an acetyl moiety, preferably acetophenone. Thus the invention is applicable to the preparation of diketones which may be generally described as noted in U.S. Pat. No. 4,175,012, noted earlier in the Related Art section above, the description of which is hereby incorporated by reference. The preferred diketone may be generally described as 1-phenyl or 1-(alkyl substituted phenyl)alkane-1,3-dione in which the alkyl group may have up to about 18 carbon atoms, and in which the alkane group may contain from 4 up to about 20 carbon atoms.

In the preferred embodiment of this invention, acetophenone is reacted with the methyl ester of isooctanoic acid, which results in the 1-phenyl isodecane- 1,3-dione product.

As indicated the lower alkyl (1 to about 4 carbon atoms) esters of alkanoic (up to about 18 carbon atoms) acids are preferably reacted with acetophenone or an alkylated acetophenone. The reaction is an alkaline condensation reaction carried out in the presence of an alkaline catalyst and an inert organic solvent. The preferred diketones are the phenyl, or alkyl substituted phenyl, alkane diones, in which the alkyl group may contain up to about 18 carbon atoms, and the alkane group may contain from 4 up to about 20 carbon atoms.

It has now been discovered that the disadvantages of the current process for preparation of the diketones, particularly 1-phenyl isodecane-1,3-dione, can be overcome by the present invention, which will result in optimization of the yield and minimization of degradation resulting during the reaction.

The overall process to produce the diketone comprises the (a) addition of the acetophenone to the reaction vessel containing the ester, the alkaline catalyst, preferably sodium methoxide, and the organic solvent, (b) completion of the reaction at elevated temperature (i.e. reflux temperature), (c) rapid cooling by the addition of more solvent, (d) acidification of the resultant reaction product mixture to acidify any sodium salts, and washing of the resultant organic solvent phase containing the diketone, and (e) recovery of the diketone by removal of the volatiles and distillation under vacuum to provide the diketone.

It was found that four aspects of the process must be considered to maximize the yield and minimize degradation products in carrying out the reaction. The first aspect lies in the addition of the acetophenone to the reaction vessel, containing the ester, alkaline catalyst, preferably sodium methoxide, and the organic solvent media. It was found that in order to provide maximum production of diketone with minimum degradation products, it is necessary to add the acetophenone quickly, i.e. in a sufficiently short time to prevent or minimize degradation of the diketone in the presence of alkaline components. In the second aspect, as soon as the reaction is completed, the temperature of the reaction product mixture is rapidly decreased by adding additional solvent. The lower temperature significantly decreases the rate of degradation of product diketone. In the third aspect, acidification must be substantially complete and the washing of the organic phase containing the diketone product must be washed thoroughly so as to remove substantially all of the alkali metal salts, i.e. preferably until analysis shows substantially zero alkali metal. In the fourth aspect, it was also found that the overall process from the addition of the acetophenone through the initial acidification of the reaction product, must also be carried out in a time sufficiently short to minimize degradation products.

It was found that if the acidification is not sufficiently complete to acidify the alkali metal salts and the washing is not sufficiently complete to remove the alkali metal salts, degradation of the diketone to carboxylic acid will occur during volatiles removal and diketone distillation. For each 1% carboxylic acid formed by degradation of the diketone product, about 2% loss of yield of diketone results. Without the use of the present invention, incomplete acidification and incomplete washing can result in levels of isooctanoic acid and benzoic acid of about 15% and about 18%, respectively, in the resultant distilled product. This illustrates that the use of the present invention minimizes degradation of the diketone product and results in maximization of the yield of diketone.

The invention can be further illustrated by means of the following example.

EXAMPLE 1

This example illustrates the preparation of 1-phenylisodecane-1,3-dione by the alkaline condensation of acetophenone and methyl isooctanoate. The organic media for the reaction is toluene. In the course of the condensation reaction some of the methyl isooctanoate is converted to sodium isooctanoate. The acetophenone is added to the reaction vessel in as short a time as possible consistent with the equipment used. The condensation reaction is conducted at reflux temperatures so that the azeotrope formed by toluene with byproduct methanol or with water is continuously removed during the reaction. After the completion of acetophenone addition, the temperature of the reaction mixture is rapidly decreased by adding additional toluene. To acidify the reaction mixture after completion of the reaction in as short a time as possible, the entire mixture is transferred in as short a time as possible to another stirred reactor which contains excess aqueous sulfuric acid, whereby the sodium salts are acidified.

The sulfuric acid is present in an amount sufficient to provide a pH of about 2 to the aqueous phase after all the condensation product mixture has been transferred and thoroughly mixed. The resultant acidified organic phase is washed with water several times to remove salts and excess acid. The first exiting wash water has a pH of about 2–3, and the final wash a pH of about 3–4. The alkali metal content of the organic phase at this point is typically less than 1 ppm. The resultant organic phase is then stripped of volatiles at elevated temperature and reduced pressure. Then the residue is distilled at reduced pressure (vacuum). The distilled finished product, the desired diketone product, 1-phenylisodecane-1,3-dione, when subjected to gas chromatographic analysis contains no detectable isooctanoic acid or benzoic acid when acidification was complete. When complete acidification and washing, as indicated by sodium levels, was not accomplished, the finished product showed levels of isooctanoic acid of about 1 to 1.5% and benzoic acid levels of about 1 to about 1.8%.

As indicated above an organic solvent is employed as the reaction media. Any inert organic hydrocarbon solvent may be employed. Toluene, the preferred solvent is illustrated in the Example above, however, other solvents such as xylene, benzene, heptanes, octanes and the like, may be employed.

It is claimed:

1. In a process of preparing a beta-diketone comprising:
   (a) reacting an acetophenone and an ester in the presence of alkali catalyst in an inert hydrocarbon solvent at reflux temperature for the organic solvent, whereby the diketone condensation product of said acetophenone and ester is formed;
   (b) reacting the reaction product mixture with aqueous acid to produce an organic solvent phase and an aqueous acid phase whereby the alkali metal salts present in the reaction mixture are acidified;
   (c) washing the organic solvent phase containing the diketone product to remove salt and any excess acid;
   (d) stripping of volatiles from the washed organic phase at elevated temperature; and
   (e) distilling the residue under vacuum to recover the diketone product, wherein the improvement comprises one or more of:
      (i) adding the acetophenone to the reaction mixture in a time period sufficiently short whereby degradation products in the reaction mixture are minimized and the yield of diketone product is maximized;
      (ii) at the completion of the reaction, adding additional solvent to rapidly decrease the temperature of the reaction product mixture whereby degradation products in the reaction product mixture are minimized and the yield of diketone product is maximized;
      (iii) mixing the organic solvent phase with the aqueous acid phase in step (b) for a time period sufficiently long whereby the concentration of alkali metal remaining in the organic solvent phase is substantially zero; and
      (iv) decreasing the time between the completion of step (a) and the initiation of step (b) to a period sufficiently short whereby degradation products in the reaction mixture are minimized and the yield of diketone product is maximized.

2. A process as defined in claim 1 wherein the acetophenone reactant is acetophenone and the ester is the methyl ester of isooctanoic acid.

3. A process as defined in claim 1 wherein the diketone product is 1-phenylisodecane-1,3-dione.

4. A process as defined in claim 3 wherein the dione contains substantially no isooctanoic acid or benzoic acid and the alkali metal content of the product of step (c) is substantially 0.

5. A process as defined in claim 1 wherein the ester is a lower alkyl ester of an alkanoic acid having from 1 to about 4 carbon atoms in the alkyl group and up to 20 carbon atoms in the alkanoic acid.

6. A process as defined in claim 1 wherein the alkali catalyst is sodium methoxide.

* * * * *

UNITED STATES PATENT AND TRADEMARK OFFICE
CERTIFICATE OF CORRECTION

PATENT NO. : 5,457,236
DATED : Oct. 10, 1995
INVENTOR(S) : Leroy O. Krbechek, Mary I. Casey It is certified that error appears in the above-indentified patent and that said Letters Patent is hereby corrected as shown below:

In col. 3, line 3, delete [15% and about 18%] and insert --1.5% and about 1.8%--.

Title page, item: [75] Inventors, after "Mary I. Casey, Bishopstown," delete [Islamic] and insert --Cork,--.

Signed and Sealed this

Eighth Day of October, 1996

Attest:

BRUCE LEHMAN

*Attesting Officer*   *Commissioner of Patents and Trademarks*